US009089454B2

(12) United States Patent
Mattingly et al.

(10) Patent No.: US 9,089,454 B2
(45) Date of Patent: Jul. 28, 2015

(54) ABSORBENT ARTICLE HAVING A FUNCTIONAL AND PARTIALLY ENCIRCLING WAISTBAND

(75) Inventors: Walter Andrew Mattingly, Appleton, WI (US); Sherry A. VanDyke, Neenah, WI (US); Michael Donald Sperl, Waupaca, WI (US); Lisa L. Bushman, Kaukauna, WI (US); Robert Lee Popp, Hortonville, WI (US); Valerie V. Finch, Neenah, WI (US); Thomas E. Williamson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 942 days.

(21) Appl. No.: 11/956,986

(22) Filed: Dec. 14, 2007

(65) Prior Publication Data
US 2009/0157034 A1 Jun. 18, 2009

(51) Int. Cl.
A61F 13/49 (2006.01)
A61F 13/56 (2006.01)

(52) U.S. Cl.
CPC ..... A61F 13/49014 (2013.01); A61F 13/49011 (2013.01); A61F 13/5622 (2013.01); A61F 2013/5683 (2013.01)

(58) Field of Classification Search
CPC ............ A61F 13/49011; A61F 13/49012; A61F 13/49014
USPC ............ 604/385.28, 385.27, 385.3, 385.29
See application file for complete search history.

(56) References Cited

U.S. PATENT DOCUMENTS

| 3,734,101 A | 5/1973 | La Cascio |
| 4,100,324 A | 7/1978 | Anderson et al. |
| 4,323,534 A | 4/1982 | Des Marais |
| 4,655,760 A | 4/1987 | Morman et al. |
| 4,657,802 A | 4/1987 | Morman |

(Continued)

FOREIGN PATENT DOCUMENTS

| EP | 0217032 | 4/1987 |
| WO | WO0037009 A2 | 6/2000 |
| WO | WO0188245 A2 | 11/2001 |

OTHER PUBLICATIONS

International Search Report PCT/IB2008/053891, dated Apr. 16, 2009.

(Continued)

Primary Examiner — Melanie Hand
Assistant Examiner — Paula L Craig
(74) Attorney, Agent, or Firm — Dority & Manning, P.A.

(57) ABSTRACT

Absorbent articles are disclosed having extended waistbands. More particularly, the absorbent articles include a back waistband and/or a front waistband that encircle a portion of the circumference of the waist opening. The absorbent article includes a front portion attached to a back portion by a pair of stretchable side areas. Each of the side areas are made from at least two panels that are connected together along a vertical attachment area. In accordance with the present disclosure, a waistband is incorporated into the article that extends over the entire front portion or the entire back portion and terminates at opposite ends on opposing side areas. Each end of the waistband, however, terminates prior to the vertical attachment areas leaving a gap in between. The presence of the gap has been found to provide various benefits and advantages including improved stretch properties for donning the article.

18 Claims, 6 Drawing Sheets

(56) References Cited

U.S. PATENT DOCUMENTS

| | | | |
|---|---|---|---|
| 4,663,220 A | 5/1987 | Wisneski et al. | |
| 4,704,116 A | 11/1987 | Enloe | |
| 4,720,415 A | 1/1988 | Vander Wielen et al. | |
| 4,743,239 A * | 5/1988 | Cole | 604/385.23 |
| 4,781,966 A | 11/1988 | Taylor | |
| 4,787,699 A | 11/1988 | Moulin | |
| 4,789,699 A | 12/1988 | Kieffer et al. | |
| 4,808,252 A * | 2/1989 | Lash | 156/73.1 |
| 4,834,739 A | 5/1989 | Linker, III et al. | |
| 4,909,804 A * | 3/1990 | Douglas, Sr. | 604/385.29 |
| 4,937,299 A | 6/1990 | Ewen et al. | |
| 4,940,464 A | 7/1990 | Van Gompel et al. | |
| 4,965,122 A | 10/1990 | Morman | |
| 4,981,747 A | 1/1991 | Morman | |
| 5,046,272 A | 9/1991 | Vogt et al. | |
| 5,069,678 A * | 12/1991 | Yamamoto et al. | 604/385.21 |
| 5,104,116 A | 4/1992 | Pohjola | |
| 5,114,781 A | 5/1992 | Morman | |
| 5,116,662 A | 5/1992 | Morman | |
| 5,218,071 A | 6/1993 | Tsutsui et al. | |
| 5,224,405 A | 7/1993 | Pohjola | |
| 5,226,992 A | 7/1993 | Morman | |
| 5,242,436 A * | 9/1993 | Weil et al. | 604/385.29 |
| 5,272,236 A | 12/1993 | Lai et al. | |
| 5,278,272 A | 1/1994 | Lai et al. | |
| 5,284,703 A | 2/1994 | Everhart et al. | |
| 5,304,599 A | 4/1994 | Himes | |
| 5,332,613 A | 7/1994 | Taylor et al. | |
| 5,336,545 A | 8/1994 | Morman | |
| 5,350,624 A | 9/1994 | Georger et al. | |
| 5,383,871 A * | 1/1995 | Carlin et al. | 604/385.29 |
| 5,397,318 A * | 3/1995 | Dreier | 604/385.19 |
| 5,531,732 A * | 7/1996 | Wood | 604/391 |
| 5,539,056 A | 7/1996 | Yang et al. | |
| 5,593,401 A | 1/1997 | Sosalla et al. | |
| 5,596,052 A | 1/1997 | Resconi et al. | |
| 5,645,524 A | 7/1997 | Doyle | |
| 5,672,164 A | 9/1997 | Crane | |
| 5,827,259 A | 10/1998 | Laux et al. | |
| 5,957,907 A * | 9/1999 | Sauer | 604/385.24 |
| D437,932 S * | 2/2001 | Ruman et al. | D24/126 |
| D438,614 S * | 3/2001 | Ratliff et al. | D24/126 |
| 6,210,388 B1 * | 4/2001 | Widlund et al. | 604/390 |
| 6,336,922 B1 * | 1/2002 | VanGompel et al. | 604/385.3 |
| 6,352,528 B1 * | 3/2002 | Weber et al. | 604/385.03 |
| 6,362,389 B1 | 3/2002 | McDowall et al. | |
| 6,432,248 B1 * | 8/2002 | Popp et al. | 156/256 |
| 6,500,563 B1 | 12/2002 | Datta et al. | |
| 6,552,245 B1 | 4/2003 | Roessler et al. | |
| 6,592,562 B2 * | 7/2003 | Menard et al. | 604/385.04 |
| 6,645,190 B1 | 11/2003 | Olson et al. | |
| 6,761,711 B1 | 7/2004 | Fletcher et al. | |
| 6,849,067 B2 | 2/2005 | Fletcher et al. | |
| 6,969,377 B2 | 11/2005 | Koele et al. | |
| 6,969,378 B1 | 11/2005 | Vukos et al. | |
| 7,220,251 B2 * | 5/2007 | Otsubo et al. | 604/385.201 |
| 7,462,172 B2 * | 12/2008 | Wright et al. | 604/385.03 |
| 7,704,589 B2 | 4/2010 | Olson et al. | |
| 8,147,475 B2 * | 4/2012 | Suzuki et al. | 604/385.24 |
| 2001/0016719 A1 * | 8/2001 | Mishima | 604/385.19 |
| 2001/0049516 A1 * | 12/2001 | Shimada et al. | 604/385.11 |
| 2002/0151863 A1 * | 10/2002 | Toyoshima | 604/385.29 |
| 2002/0173767 A1 * | 11/2002 | Popp et al. | 604/387 |
| 2002/0173768 A1 * | 11/2002 | Elsberg et al. | 604/391 |
| 2003/0069557 A1 | 4/2003 | Driskell et al. | 604/385.3 |
| 2003/0114826 A1 * | 6/2003 | Roessler et al. | 604/385.28 |
| 2003/0114828 A1 * | 6/2003 | Minato | 604/389 |
| 2004/0225271 A1 * | 11/2004 | Datta et al. | 604/385.11 |
| 2004/0243090 A1 * | 12/2004 | Toyoshima et al. | 604/389 |
| 2005/0027271 A1 * | 2/2005 | Popp et al. | 604/385.01 |
| 2005/0043701 A1 | 2/2005 | Otsubo et al. | |
| 2005/0080394 A1 * | 4/2005 | Otsubo et al. | 604/385.27 |
| 2005/0131379 A1 * | 6/2005 | Otsubo et al. | 604/387 |
| 2005/0256489 A1 * | 11/2005 | Sawyer et al. | 604/385.23 |
| 2007/0038199 A1 * | 2/2007 | Erdman et al. | 604/385.3 |
| 2007/0142806 A1 * | 6/2007 | Roe et al. | 604/385.01 |
| 2007/0250029 A1 | 10/2007 | Popp et al. | |
| 2008/0154227 A1 * | 6/2008 | Andersson et al. | 604/385.22 |
| 2008/0312631 A1 * | 12/2008 | Okuda | 604/385.23 |
| 2010/0137823 A1 | 6/2010 | Corneliusson et al. | |

OTHER PUBLICATIONS

EP Search Report, Jan. 28, 2013.

* cited by examiner

ABSORBENT ARTICLE HAVING A FUNCTIONAL AND PARTIALLY ENCIRCLING WAISTBAND

BACKGROUND

Disposable absorbent garments such as adult incontinence products, diapers, training pants, swim pants, fitted briefs, feminine hygiene products, and the like conventionally include a liquid permeable body-facing liner, a liquid impermeable outer cover, and an absorbent core. The absorbent core is typically located in between the outer cover and the liner for taking in and retaining liquids, such as urine, exuded by the wearer.

In many embodiments, the disposable garments may contain various elastic materials to permit some expansion of the article when necessary and/or to provide a better fit on the wearer. For example, some absorbent garments have been made in the past containing waist elastic members that allow portions of the waist of the article to expand and contract. Absorbent garments have also been made with elastic side panels that allow the garments to expand around the hip and leg of a wearer.

Although the use of various elastics in disposable absorbent garments have provided improved products, further improvements are still needed. For example, when designing training pants, swim pants, and adult incontinence products, some users desire for the disposable absorbent garments to look and feel like underwear. Thus, various attempts have been made in the past to include encircling waistbands. The present disclosure is directed to an absorbent article that has a substantially encircling waistband for providing better fit and comfort as will be described in greater detail below.

SUMMARY

In general, the present disclosure is directed to disposable absorbent articles that have at least one waistband that partially encircles the front, the back or both the front and back of the wearer. As will be described in detail below, the waistband not only improves the look and feel of the article, but is incorporated into the article in a manner that provides other various benefits and advantages. The manner in which the waistband is incorporated in the article also allows for various process advantages during construction of the article.

In one embodiment, for instance, the present disclosure is directed to an absorbent article that comprises a chassis defining a waist opening opposite two leg openings. The chassis contains an absorbent core and includes a front portion, a back portion, and a crotch portion positioned in between the front portion and the back portion. The chassis further includes first and second opposing stretchable side areas. The first side area, for instance, can include a first panel attached to a second panel along a first vertical attachment area. Similarly, the second side area can also be constructed from two different panels that are also joined together along a second vertical attachment area. The panels that comprise the first and second side areas can be separate pieces of material attached to the chassis or can be integral with the chassis.

In accordance with the present disclosure, the absorbent article further includes a back waistband that partially encircles the waist opening of the chassis. The back waistband has a first end and a second and opposite end. The first end of the back waistband terminates on the first side panel of the first side area but leaves a gap between the first end and the first vertical attachment area. Similarly, the second end of the back waistband terminates on the first side panel of the second side area while also leaving a gap between the second end and the second vertical attachment area.

The gap between the ends of the back waistband and the first and second vertical attachment areas respectively can vary depending upon the particular application. In one embodiment, for instance, the gap may be from about 3 mm to about 80 mm, such as from about 10 mm to about 50 mm. The gap formed between the ends of the back waistband and the first and second vertical attachment areas provides various advantages and benefits while still providing a substantially encircling waistband. For example, the gap between the ends of the waistband and the first and second vertical attachment areas allows for a low tension, higher stretch area over the side areas. This low tension, high stretch area allows for greater ease of donning, improved comfort, and potentially increases the acceptable weight or size range of the product. The gaps between the ends of the waistband and the vertical attachment areas also provide for a natural folding area when packaging the product and allows for the product to be more efficiently made.

In addition to a back waistband, the absorbent article may include a similar front waistband alone or in combination with the back waistband. When used in combination with the back waistband, the waistbands together almost completely encircle the product. When a front waistband is present, the front waistband includes a first end and a second and opposite end. The first end of the front waistband can terminate on the second side panel of the first side area while leaving a gap as described above between the first vertical attachment area and the first end. The second end of the front waistband can terminate on the second side panel of the second side area and can also define a gap between the second end and the second vertical attachment area.

The vertical attachment areas on the side areas can vary depending upon the particular product. For instance, in one embodiment, the vertical attachment areas can comprise permanent attachments between the panels that make up the side areas. For instance, the first and second vertical attachment areas may comprise seams where the ends of the panels have been thermally bonded, ultrasonically bonded, pressure bonded, and/or adhesively bonded.

Alternatively, the first and second vertical attachment areas may comprise releasable attachment fasteners that allow for the chassis to assume an open and unfolded configuration when the ends of the panels that make up the side areas are disengaged from one another. In this embodiment, for instance, the releasable attachment fastener may comprise a mechanical fastener, such as a hook and loop fastener or an adhesive fastener.

The side areas, the back waistband and the front waistband are all made from at least stretchable materials, such as elastic materials. In one embodiment, for instance, the side areas and the waistbands can be made from a material that includes an elastic film, an elastic nonwoven web, or an elastic woven web. In one particular embodiment, the side areas, the back waistband, and the front waistband are all made from elastic laminates, such as stretch bonded laminates. The stretch bonded laminate may include, for instance, an elastic layer positioned in between two gathered layers.

In one embodiment, the entire chassis can be made from stretchable materials, such as elastic materials. For instance, the chassis can have a one-piece construction such that the side areas are integral with the front portion and back portion of the chassis. The chassis, for instance, can include an outer cover, a liner, and an absorbent core positioned in between the outer cover and the liner. When the chassis is made from stretchable materials, such as elastic materials, for instance, the liner, the outer cover, or both the liner and the outer cover can be made so as to have stretch or elastic characteristics.

As described above, the ends of the back waistband extend over and can attach to the first and second side areas. The side areas, for instance, can have a defined length that extends in the lateral direction of the chassis. The ends of the back waistband can extend over at least about 25% of the length of the first panel of each side area. For instance, in one embodiment, the ends of the back waistband can extend over at least about 30% of the length of the respective side panels, while still forming a gap between each end and each vertical attachment area.

The back waistband and the front waistband can lie adjacent to the interior surface of the chassis so as to be positioned adjacent to the body of a wearer. Alternatively, the waistbands can lie on the exterior surface of the chassis. In still another embodiment, the waistbands can be at least partly incorporated into the chassis construction. For instance, in one embodiment, at least a portion of the back waistband and/or the front waistband can be positioned in between the liner and the outer cover that comprise the chassis.

The front and back waistbands can also be positioned adjacent to a waist edge of the chassis. The front and/or back waistband can also have a width that is less than the width of the side areas. For instance, each of the side areas and the waistbands can have a width that extends in the longitudinal direction of the chassis. The one or more waistbands can have a width that is less than about 125% of the width of the side panels. For instance, in one embodiment, the back waistband can have a width that is from about 15% to about 40% of the width of the side panels.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present disclosure is directed to an absorbent article having an extended waistband. The extended waistband, for instance, may be located along the back of the article or may be located along the front of the article. In a further alternative embodiment, the absorbent article can include an extended waistband in the back of the article and in the front of the article such that the waistbands substantially encircle the waist opening.

Absorbent articles made in accordance with the present disclosure generally include a chassis defining two leg openings opposite a waist opening. The chassis, for instance, can include a front portion, a back portion, and a crotch portion positioned in between the front portion and the back portion. The chassis may further include a pair of opposing side areas that connect the front portion to the back portion around the waist opening and form a portion of the leg openings. The side areas can comprise separate pieces of material that are attached to the front and back portions or can be integral with the front and back portions. The side areas are generally made from a stretchable material. For instance, in one embodiment, the side areas can be made from an elastic material. The side areas are present on the absorbent article in order to accommodate different sizes and in order to improve the fit of the article.

The side areas present on the absorbent article are typically made from two separate panels that are attached together. The panels, for instance, may be permanently bonded together, thus forming vertical seams that extend from the waist opening to the leg openings. Alternatively, the panels that make up the side areas can be releasably attached together. For instance, in one embodiment, the two panels that make up a side area can be attached together using a suitable mechanical fastener, such as a hook and loop fastener or an adhesive fastener.

The present disclosure, as described above, is directed to incorporating one or more extended waistbands that extend around the back portion of the chassis, around the front portion of the chassis, or around both the front portion and the back portion of the chassis.

Waistbands constructed according to the present disclosure, however, only partially extend over the side areas. A fully encircling waistband that extends over the entire length of the side areas, for instance, can present various construction problems during the formation of the absorbent article and can later create various problems in the product. For instance, a fully encircling waistband may prevent the production of an absorbent article having refastenable side areas. In addition, a fully encircling waistband can create a weaker side seam in the finished product. In this regard, the present disclosure is directed to absorbent articles having a front and/or back waistbands that extend to just short of where the refastenable fasteners are located on the side area or to where the two panels that make up a side area are seamed together. By having the waistband extend over a portion of the side areas, absorbent articles can be produced according to a more efficient process with fewer defects and better side seam performance and fit. More particularly, leaving a gap between the end of the waistband and a side seam on a side area allows for a low tension, high stretch area. This low tension, high stretch area allows for greater ease of donning, improved comfort, and potentially increases the acceptable weight or size range of the product.

Figure 1:
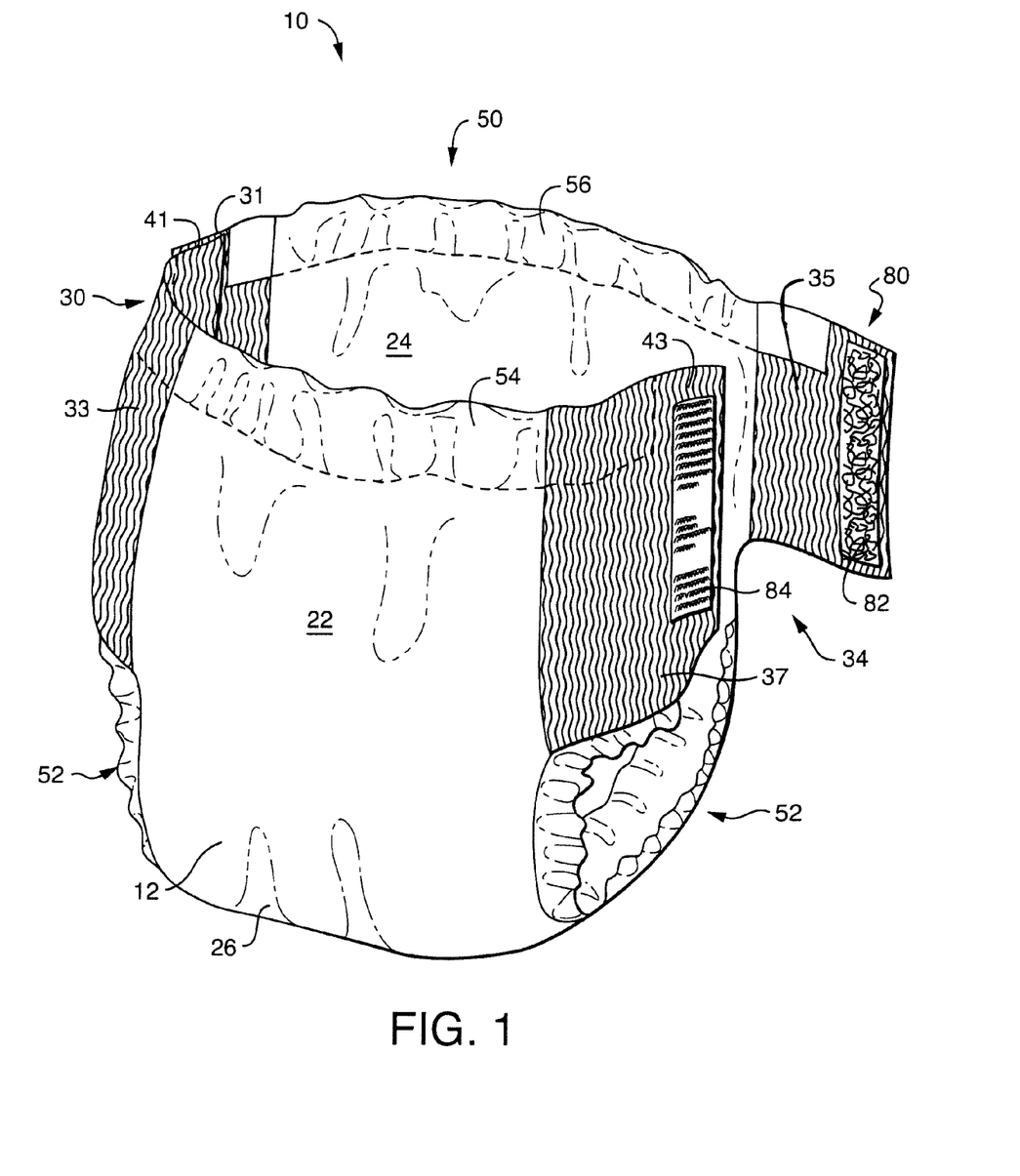
FIG. 1 is a perspective view of one embodiment of an absorbent article made in accordance with the present disclosure.
Figure 3:
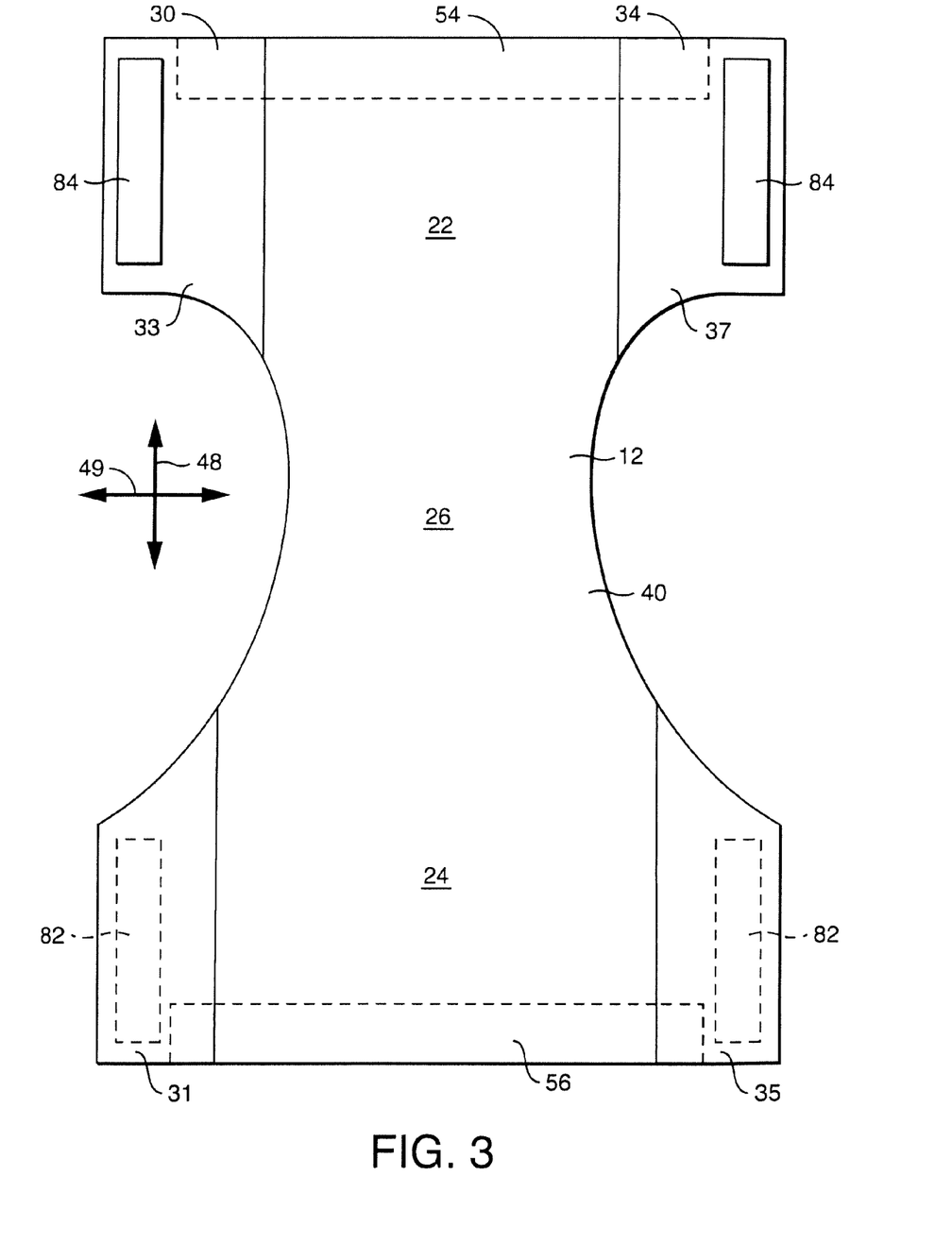
FIG. 3 is a plan view of the absorbent article illustrated in FIG. 1.
Figure 4:
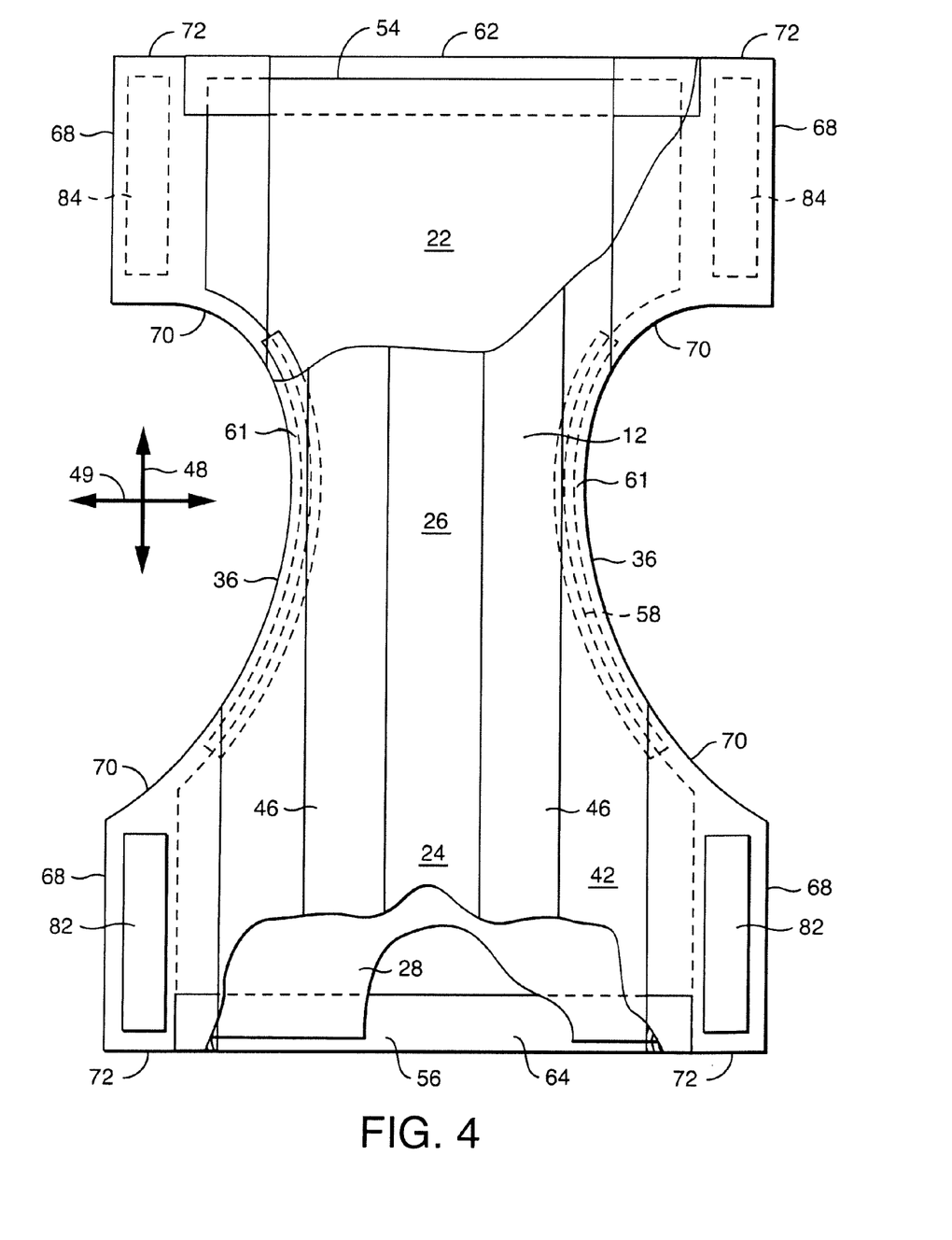
FIG. 4 is a plan view of the opposite side of the absorbent article illustrated in FIG. 3.

Referring to FIG. 1, for instance, one embodiment of an absorbent article generally 10 made in accordance with the present disclosure is shown. The absorbent article illustrated in FIG. 1 generally represents a training pant. The teachings of the present disclosure, however, may be equally applicable to other absorbent articles, such as swim pants, adult incontinence products, feminine hygiene products, and the like. The absorbent article 10 illustrated in FIG. 1 is also represented in FIGS. 3 and 4 in an opened and unfolded state. Specifically, FIG. 3 is a plan view illustrating the exterior side of the absorbent article, while FIG. 4 illustrates the interior side of the absorbent article, which is intended to rest adjacent to the wearer. As shown in FIGS. 3 and 4, as used herein, the longitudinal direction 48 extends from the front of the absorbent article to the back of the absorbent article. Opposite to the longitudinal direction 48 is a lateral direction 49.

The absorbent article 10 includes a chassis 12 that is comprised of a front portion 22, a back portion 24, and a crotch portion 26. Positioned within the crotch portion 26 and extending from the front portion 22 to the back portion 24 is an absorbent core 28 as shown in FIG. 4.

The absorbent article 10 defines an interior surface that is configured to be placed adjacent to the body when being worn. The absorbent article 10 also includes an exterior surface opposite the interior surface. The front and back portions 22 and 24 are those portions of the article which, when worn, partially cover or encircle the waist or mid-lower torso of the wearer. The crotch portion 26, on the other hand, is generally positioned between the legs of the wearer when the absorbent article has been donned.

As shown in FIG. 1, the absorbent article further includes a first side area 30 and a second side area 34. The side areas 30 and 34 connect the front portion 22 with the back portion 24. The side areas 30 and 34 can also help define the leg openings and the waist opening.

The side areas 30 and 34, in one embodiment, can be made from a stretchable or extensible material. In one embodiment, for instance, the side areas 30 and 34 are made from an elastic material. The side areas serve to form a snug but comfortable fit around the torso of a wearer. The side areas 30 and 34 can also allow for accommodating different torso circumferences.

As shown, each of the side areas 30 and 34 can be made from multiple stretchable panels. For instance, in the embodiment shown in FIG. 1, the side areas 30 and 34 are each made from two panels. As shown, for instance, the side area 30 includes a first panel 31 and a second panel 33. Similarly, the second side area 34 includes a first panel 35 attached to a second panel 37. The panels 31 and 33 of the first side area 30 are attached together to form a first vertical attachment area 41 while the panels 35 and 37 of the second side area 34 are attached together along a second vertical attachment area 43. The attachment between the panels can be permanent or can be unfastenable and refastenable. When the panels are releasably attached together, for instance, any suitable mechanical fastener may be used. For example, in one embodiment, the panels may be releasably attached together using any suitable adhesive fastener, cohesive fastener, mechanical fastener, or the like. Suitable mechanical fastening elements can be provided by interlocking geometric shaped materials, such as hooks, loops, bulbs, mushrooms, arrowheads, balls on stems, male and female mating components, buckles, snaps, and the like.

In the embodiment illustrated in FIGS. 1, 3 and 4, the panels 31 and 33 that comprise the first side area 30 and the panels 35 and 37 that comprise the second side area 34 are joined together using a fastening system 80 that includes laterally opposite first fastening components 82 adapted for refastenable engagement to corresponding second fastening components 84. For instance, in one embodiment, a front or outer surface of each of the fastening components 82, 84 includes a plurality of engaging elements. The engaging elements of the first fastening components 82 are adapted to repeatably engage and disengage corresponding engaging elements of the second fastening components 84 to releasably secure the absorbent article in its 3-dimensional configuration.

In the embodiment illustrated in FIGS. 1, 3 and 4, for instance, the first fastening components 82 include loop fasteners and the second fastening components 84 include complementary hook fasteners. Alternatively, the first fastening components 82 may include hook fasteners and the second fastening components 84 may be complementary loop fasteners. In another aspect, the fastening components 82 and 84 can be interlocking similar surface fasteners, or adhesive or co-adhesive fastening elements such as an adhesive fastener and an adhesive-receptive landing zone or material.

As particularly shown in FIG. 1, in this embodiment, the side panel 35 of the absorbent article 10 overlaps the side panel 37 along the vertical attachment area 41. Alternatively, however, the side panel 37 may overlap the side panel 35. One skilled in the art will recognize that the shape, density and polymer composition of the hooks and loops may be selected to obtain the desired level of engagement between the fastening components 82 and 84. Suitable fastening systems are also disclosed in PCT Patent Application Publication No. WO 00/37009 published on Jun. 29, 2000 and in U.S. Pat. No. 6,645,190, which are both incorporated herein by reference.

In the embodiment illustrated in FIG. 1, the loop material 82 and the hook material 84 comprise separate components that are attached to the side panels. In other embodiments, however, it should be understood that the hook material and/or the loop material may be integral with the side panels. For instance, in one embodiment, the side panel 35 can be made from a facing layer that is not only stretchable, but is also capable of engaging a hook material. For example, in one embodiment, the side panel 35 can include a facing layer comprising a spunbond web. In one embodiment, in order to improve engagement with the hook material, the spunbond web can be subjected to a bonding pattern using pressure bonding, thermal bonding, or ultrasonic bonding.

As described above, in an alternative embodiment, the panels that comprise the side areas may be permanently attached together. For instance, referring to FIG. 2, an alternative embodiment of an absorbent article 10 is shown. Like reference numerals have been used to indicate the same or similar elements. As shown, the absorbent article 10 in FIG. 2 includes a first side area 30 comprised of panels 31 and 33 and a second side area 34 comprised of panels 35 and 37. The first side panel 30 defines a first vertical attachment area 41 where the panels 31 and 33 are permanently bonded together. Similarly, the second side area 34 defines a second vertical attachment area 43 where the panels 35 and 37 have been permanently attached together. In this embodiment, the vertical attachment areas comprise seams. The seams, for instance, can be constructed in any suitable manner. For instance, the vertical seam may comprise a lap seam, a butt seam, or any other suitable configuration. The seams can be formed by attaching the panels together using any suitable method or technique. For example, the panels can be permanently attached together using ultrasonic bonding, thermal bonding, adhesive bonding, and/or pressure bonding. In still another alternative embodiment, the separate panels can be sewn together.

Figure 2:
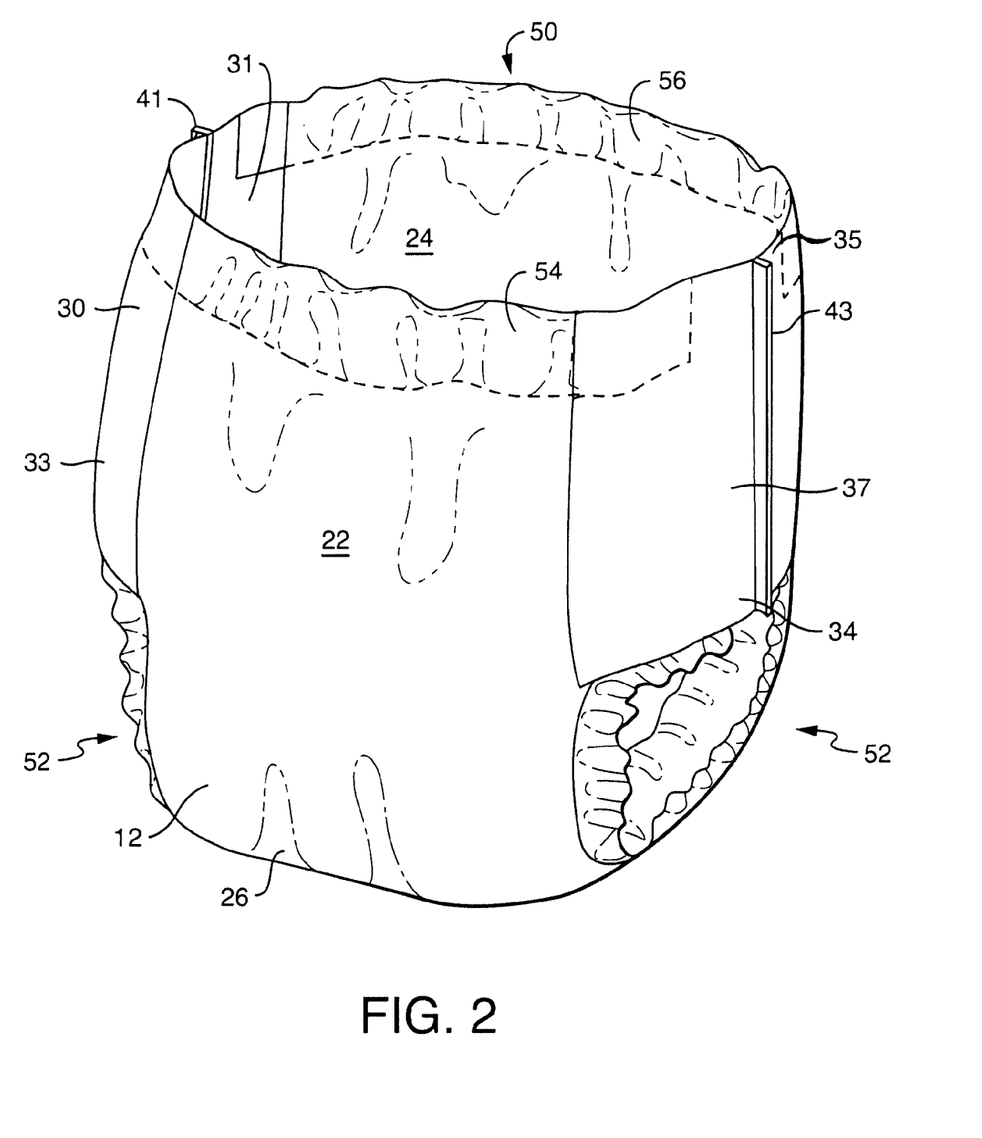
FIG. 2 is a perspective view of another embodiment of an absorbent article made in accordance with the present disclosure.

In the embodiments illustrated in FIGS. 1 and 2, the side areas 30 and 34 are comprised of different materials that are attached to the front portion 22 and the back portion 24 of the chassis. The side areas 30 and 34 can be attached to the chassis using any of the techniques described above such as ultrasonic bonding, thermal bonding, adhesive bonding, and/or pressure bonding. In an alternative embodiment, however, the side areas 30 and 34 can be integral with the front portion 22 and the back portion 24. In this embodiment, for instance, the liner and/or outer cover of the chassis can be constructed from a single piece of material.

Figure 6:
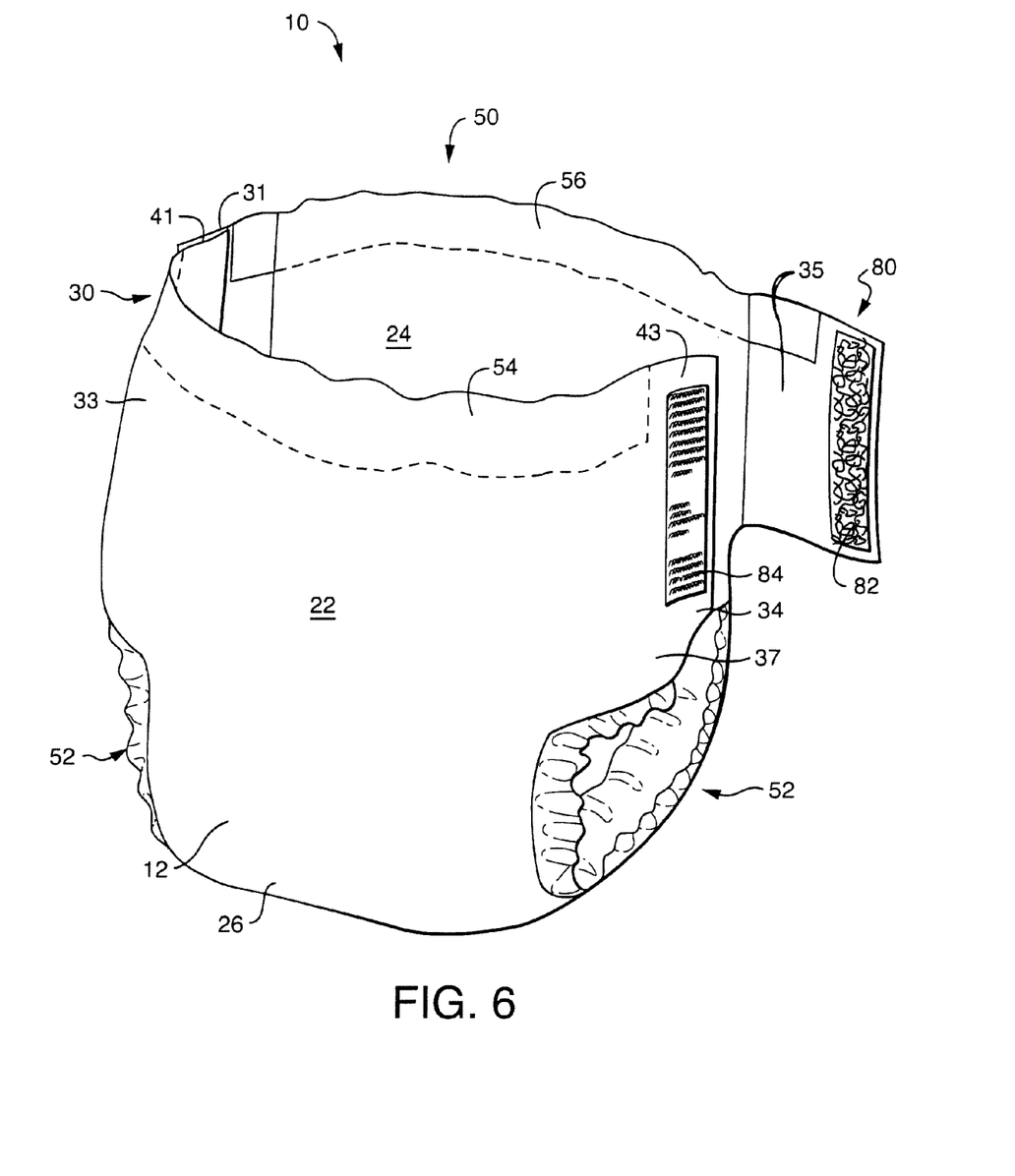
FIG. 6 is a perspective view of still another embodiment of an absorbent article made in accordance with the present disclosure.

For example, referring to FIG. 6, an embodiment of an absorbent article 10 is shown in which the liner and outer cover of the article have a one-piece construction. Like reference numerals have been used to indicate the same or similar elements. As shown, the absorbent article 10 in FIG. 6 includes a first side area 30 that is integral with a front portion 22 and a back portion 24. The absorbent article 10 also includes a second side area 34 that is also integral with the front portion 22 and the back portion 24. The embodiment illustrated in FIG. 6 is similar to the embodiment illustrated in FIG. 1 in that each side area is comprised of panels that are releasably attached together.

In the embodiment illustrated in FIG. 6, the entire chassis 12 can be constructed from a stretchable material, such as an elastic material. The stretch and/or elastic properties of the chassis can be uniform over the surface area of the chassis or can be altered in certain locations. The stretch properties of the chassis, for instance, can be altered by forming bond lines or using any other suitable technique.

As shown in FIGS. 1, 2, and 6 when the side areas 30 and 34 are in a fastened position, the front and back portions 22 and 24 are connected together to define a 3-dimensional pants configuration having a waist opening 50 and a pair of leg openings 52. The side areas 30 and 34, upon wearing of the absorbent article 10, thus include the portions of the article which are positioned on the hips of the wearer and, in one embodiment, define the upper edge of the leg openings 52. For example, in the embodiment illustrated in FIGS. 1, 2 and 6, the side areas 30 and 34 account for at least about 15%, such as at least about 20%, of the circumference of the leg openings 52.

As described above, the chassis 12 can, in one embodiment, include an outer cover 40 and a bodyside liner 42 as shown particularly in FIGS. 3 and 4. Depending upon the embodiment, the outer cover 40 and the bodyside liner 42 can comprise a unitary single-piece of material or can comprise multiple pieces of material bonded together. The bodyside liner 42 may be joined to the outer cover 40 in a superimposed relation using, for instance, adhesives, ultrasonic bonds, thermal bonds, pressure bonds or other conventional techniques. The liner 42 may suitably be joined to the outer cover 40 along the perimeter of the chassis 12 to form a front waist seam 62 and a back waist seam 64. The liner 42 may also be joined to the outer cover 40 to form a pair of side seams 61. The liner 42 can be generally adapted, i.e., positioned relative to the other components of the absorbent article 10, to be disposed toward the wearer's skin when donned. As described above, the chassis 12 also includes the absorbent core 28 which is disposed between the outer cover 40 and the bodyside liner 42 for absorbing liquid body exudates exuded by the wearer.

In accordance with the present disclosure, the absorbent article 10 further includes one or more extended waistbands that are intended to improve product appearance, to improve fit, and/or make the product feel more like real underwear. As shown in the figures, for instance, the absorbent article 10 can include a back waistband 56, a front waistband 54, or can include both a front waistband and a back waistband. As shown, for instance, the back waistband 56 extends over the entire back portion 24 of the chassis 12 and terminates at each end on the side areas 30 and 34.

Figure 5:
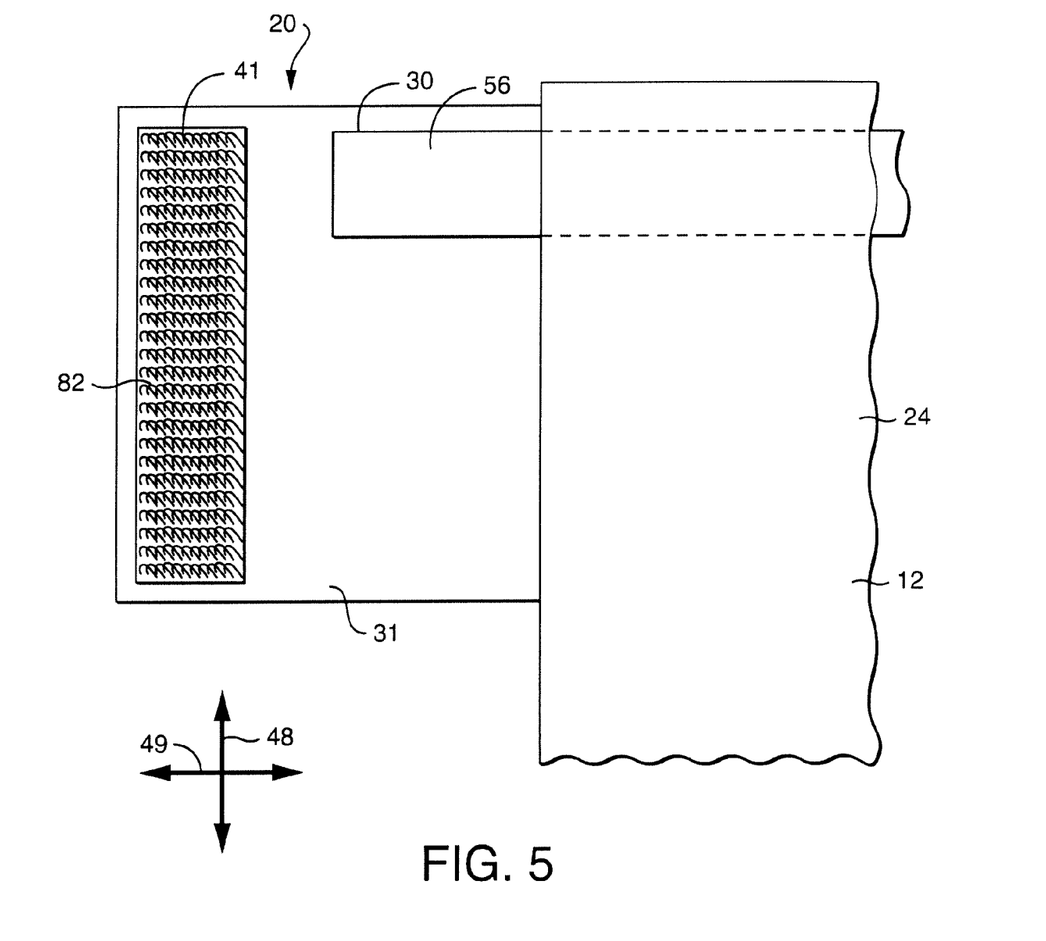
FIG. 5 is a plan view with cutaway portions illustrating the relationship between a waistband and a side area on the absorbent article illustrated in FIG. 1.

For example, referring to FIG. 5, an enlarged view of the back waistband 56 is illustrated. In the embodiment illustrated in FIG. 5, the panel 31 is rectangular in shape and does not include a curved portion as shown in the embodiments of FIGS. 3 and 4. In addition, in FIG. 5, the side panel 31 includes a hook material 82 as opposed to a loop material shown in FIGS. 1 and 6. As shown, the waistband 56 extends over the back portion 24 of the chassis 12 onto the panel 31 of the side area 30. The end of the waistband 56, however, terminates and leaves a space in between the end of the waistband and the first vertical attachment area 41 where the fastener 82 is positioned. The present inventors have discovered that creating a gap 20 between the end of the waistband 56 and the vertical attachment area 41 not only allows for the use of an extended waistband but provides various other benefits and advantages.

For example, if the waistband 56 were to extend into the vertical attachment area 41, the waistband may create a number of product and process related issues. For example, if the waistband 56 were to extend over the vertical attachment area 41, the waistband would add at least one extra layer to the vertical attachment area on the side area. The one or more extra layers may create a step change in material thickness along the length of the vertical attachment area. This step change may create difficulties in the ability to create a vertical attachment area with consistent strength along the entire vertical length of the seam. Bond strengths, for instance, may be weakest where the materials are at a minimum thickness. A weakness, for instance, along the vertical attachment area above or below a transition point resulting from the inclusion of the waistband may result in an area prone to tearing and failure. Multiple layers of material along the vertical attachment area can also create an area of increased material layers or "lump" on the product along the waist opening, thus preventing the side area from laying flat against the wearer. Any such lump may not only adversely affect the appearance of the product, but may also be uncomfortable for the user, especially when worn under clothing which may exert extra pressure against any lump that is present.

In addition to making it difficult to create a vertical attachment area with uniform properties, extending a waistband over the vertical attachment area can also make it more difficult to manipulate the panels of the side area to properly position them for attachment. For instance, an increase in thickness along the vertical attachment area at one end of the side area may cause the material to behave differently during folding and during attachment due to differences in material flexibility and thickness, thus increasing the difficulty of properly aligning the two panels together. Additional problems may also be faced when the side areas are releasably attached, such as when the side areas incorporate mechanical fasteners, such as hook and loop fasteners. The presence of the waistband within the vertical attachment area, for instance, may result in inconsistent and non-uniform attachment strength along the length of the mechanical fastener. The presence of the waistband may also make it difficult to incorporate a hook material or a loop material onto the side areas.

Thus, the present disclosure is directed to using an extended waistband that is nearly fully encircling along the waist opening. As shown in the drawings, for instance, one or more waistbands may be incorporated into the product in a manner such that the waistbands extend onto the side areas 30 and 34, but without fully extending into the vertical attachment area. Instead, as shown in FIG. 5, a gap 20 is formed between the end of the waistband and the vertical attachment area. The presence of the gap 20 can avoid all of the disadvantages as described above. The presence of the gap, for instance, allows for the formation of a vertical attachment area having a uniform thickness. The uniform thickness facilitates the formation of a seam if the attachment of the panels together is permanent and facilitates placing releasable fasteners on the panels. For example, more uniform bonding can be obtained along the vertical attachment areas. In addition, when the absorbent article includes a mechanical fastener positioned in the side areas, the more uniform thickness makes it easier to obtain uniform and good fastener engagement.

In addition, the gap 20 forms a natural hinge point in the product. The hinge point facilitates folding of the product when being packaged and also further serves to engage and disengage a refastenable fastener located along the vertical attachment areas.

Incorporation of the gap into the absorbent article also translates into various other improvements in the product itself. For instance, by including the gap 20, the risk of defects being present in the vertical attachment area is greatly reduced, resulting in stronger side seams in the product and a reduced risk of "zipper" failures.

Having the waistband terminate prior to the vertical attachment area also produces a thinner product along the side areas having more tailored side seams that lay flat against the skin of the wearer. In addition, incorporating a gap into the product allows for greater flexibility in choosing materials to construct the waistband. For instance, thicker materials, such as laminates may more easily be incorporated into the product and used to form the front waistband and/or the back waistband. Using relatively thick materials to produce the front waistband and/or the back waistband may provide various benefits and advantages. For instance, the use of thicker materials may provide for a better gasket around the waist of the material and thus better contain bodily fluids. A thicker waistband may also provide a greater cushion and softness to the user. The thickness of the waistbands, for instance, may be greater than about 0.5 mm, such as from about 0.5 mm to about 5 mm, such as from about 2 mm to about 5 mm.

Having the waistband 56 extend over the vertical attachment area 41, can also actually create unwanted tension within the product. For example, a fully encircling waistband that extends the entire length of the side areas may result in an increased product waistband opening tension that may make the product more difficult to don.

Of particular advantage, inclusion of the gap into the product also allows for better overall stretch properties around the waist opening. Having the back waistband and the front waistband terminate prior to the vertical attachment areas, for instance, provides all the benefits of a fully encircling waistband while providing tailored stretch properties within the side areas. For example, the gap 20 present within the side areas generally has greater stretch properties than the remainder of the waist opening. For instance, the gap can be constructed so as to stretch a greater amount than the area where the waistband is located for a given amount of force. This extra stretch portion makes the product easier to pull up and encircle the waist of a wearer since expansion of the side areas is not overly restricted due to the presence of the waistband. Having an extended waistband, on the other hand, that extends into the side areas can provide a better overall fit and underwear-like feel.

In order to adjust the stretch characteristics of the absorbent article and particularly in order to control the stretch characteristics of the side areas 30 and 34, the size of the gap 20 between the end of the waistband and the vertical attachment area can vary. For example, a relatively small gap may aid the fastening process in creating a natural hinge in the side areas. On the other hand, a relatively large gap may provide a greater amount of overall stretch within the side areas. The size of the gap is measured as shown in FIG. 5 from the inside edge of the fastener mechanism to the edge of the waistband.

The actual size of the gap can vary on numerous factors, particularly the size of the absorbent article and whether the absorbent article is configured to be worn by an infant, a child, or an adult. For exemplary purposes only, the gap, for instance, can generally be at least about 3 mm in length and up to about 150 mm, such as from about 10 mm to about 50 mm. A relatively narrow gap, for instance, may have a length of from about 3 mm to about 10 mm, such as from about 3 mm to about 5 mm. A relatively larger gap, on the other hand, may have a length of from about 20 mm to about 80 mm. It should be understood, however, that the above dimensions are merely exemplary and may vary depending upon the particular application and the size of the product.

The size of the gap can also be expressed where appropriate as a percentage of the lateral length of the waistband (measured at the top of the product) in relation to the functional product width in the lateral direction. The functional product width, for instance, can be measured at the top of the product from the inside edge of the fastener mechanism on one side to the inside edge of the fastener mechanism on the opposite side. For example, in some embodiments, where appropriate, the percentage of the lateral length of the waistband in relation to the functional product width can be from about 45% to about 95%. For instance, in one embodiment, the percentage difference between the lateral length of the waistband and the functional product width can be from about 45% to about 65%. In an alternative embodiment, the percentage between the lateral length of the waistband and the functional product width can be from about 80% to about 95%. When constructing a garment using the above percentages, the waistband can generally be centered about the functional product width such that the gap at each end is substantially the same.

As shown in FIG. 5, in accordance with the present disclosure, the waistband extends over at least a portion of the side panel 31 of the side area 30. For instance, referring to FIG. 5, the panel 31 of the side area 30 has a length that extends in the lateral direction 49. The length of the side panel 31, for instance, can be determined by measuring from the functional inside edge of the side panel (where the fastener is located) to where the side panel attaches to the back portion 24 of the chassis 12. When the side panel 31, however, is integral with the chassis 12, the length of the panel can be measured from the outermost edge of the absorbent core to the outermost edge of the chassis.

As shown, the waistband 56 overlaps the panel 31. In particular, the waistband 56 can overlap at least 25% of the length of the panel 31, such as at least 30% of the length, such as at least 40% of the length, such as at least 50% of the length, such as at least 60% of the length, such as even greater than about 95% of the length of the panel 31. The opposite end of the waistband 56 can also similarly overlap the opposing panel 35 of the side area 34.

As shown in the figures, in addition to the back waistband 56, the absorbent article 10 may include a similar front waistband 54 made in accordance with the present disclosure. The front waistband 54 can completely encircle the front portion 22 of the chassis 12 and also extend onto the side areas 30 and 34. In particular, the front waistband 54 can extend over and terminate on the side areas 30 and 34 respectively forming gaps between the ends of the waistband and the vertical attachment areas as described above. In addition, the front waistband 54 can overlap the side panels of the side areas in the same amounts as described above.

When the absorbent article includes a front waistband 54 in conjunction with a back waistband 56, an absorbent article is produced having a nearly encircling waistband. As described above, however, it is believed that the construction of the article and the stretch properties of the article are in fact better than if the waistband completely encircled the waist opening.

As shown particularly in FIG. 5, the waistband, in one embodiment, is narrower in longitudinal width than the side areas 30 and 34. It should be understood, however, that in other embodiments the waistband may have substantially the same width as the side areas. In the embodiment illustrated, however, the waistband has a width that is substantially less than the side areas. For instance, the waistband can have a width of from about 15 mm to about 75 mm.

In relation to the side areas 30 and 34, for instance, the waistband can have a width that is from about 10% to about 90% (or even greater) than the width of the side areas. More particularly, the waistband can have a width that is from about 15% to about 75% of the width of the side area. In one particular embodiment, for instance, the front waistband and/or the back waistband can have a width that is from about 15% to about 40% of the width of the side areas.

The front waistband 54 and/or the back waistband 56 can be incorporated into the absorbent article 10 in any suitable manner. For instance, the waistband can be directly adhered to the inside surface of the article or to the exterior surface of the article. In one embodiment, the waistbands 54 and 56 can be placed in between the bodyside liner 42 and the outer cover 40. In this embodiment, as shown in FIG. 5, when extending onto the side areas 30 and 34, the waistbands are adhered to the interior surface of the side areas. More specifically, the chassis 12 includes an interior surface that is configured to face a wearer and an exterior surface opposite the interior surface. As such, the back or front waistbands 54, 56 can be positioned adjacent to the interior surface, while the other waistband can be positioned adjacent to the exterior surface.

The waistbands can be attached to the chassis using any suitable method or technique. For instance, the waistband can be ultrasonically bonded, thermally bonded, pressure bonded, adhered to the chassis using an adhesive, or bonded using any combination thereof. Further, the waistbands can be uniformly adhered to the chassis or can be attached to the chassis at particular locations along the length of the waistband.

The waistbands 54 and 56 can be made from any suitable elastic material. For instance, the waistbands can be made from a single layer of material or can be made from a laminate containing multiple layers of material. Suitable elastic materials include sheets, strands, nonwoven webs, or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that the elastic retractive forces are imparted to the substrate.

Suitable elastic materials that may be used to form the waistbands are described in U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewith.

As used herein, a neck bonded laminate refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein, a stretch bonded laminate refers to a composite material having at least two layers in which one layer is a nonelastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. Nos. 4,789,699 to Kieffer et al., 4,781,966 to Taylor, 4,657,802 to Morman, and 4,655,760 to Morman et al., all of which are incorporated herein by reference thereto.

In one particular embodiment, for instance, the waistbands 54 and 56 can be formed from a stretch bonded laminate containing an elastic film layer or strand layer positioned in between two gathered layers that allow the elastic layer to stretch.

When containing strands, the strand layer can generally contain a plurality of elastic strands positioned in parallel. The number of strands may vary as desired, such as from 3 to about 20, in some embodiments from about 7 to about 18, and in some embodiments, from about 8 to 15 strands per cross-directional inch. The strands may have a circular cross-section, but may alternatively have other cross-sectional geometries such as elliptical, rectangular as in ribbon-like strands, triangular, multi-lobal, etc. The diameter of the strands (the widest cross-sectional dimension) may vary as desired, such as within a range of from 0.1 to about 4 millimeters, in some embodiments from about 0.2 to about 2.5 millimeters, and in some embodiments, from 0.5 to about 2 millimeters. Further, the elastic strands may generally be arranged in any direction or pattern. For example, in one embodiment, the strands are arranged in a direction that is substantially parallel to the lateral direction of the garment and are desirably spaced apart from each other at similar intervals.

If desired, the elastic strands may be substantially continuous in length so that they are in the form of filaments. Such filaments may be produced using any of a variety of known techniques, such as by extruding an elastomeric polymeric composition from a die having a series of extrusion capillaries arranged in a row. As is well known in the art, meltblown dies may be suitable for forming the filaments, except that the high velocity gas streams used in fiber attenuation are generally not employed. Rather, the molten polymer extrudate is pumped from the die capillaries and allowed to extend away from the die under the impetus of gravity. Besides extruded filaments, other elastic filaments may also be employed in the present disclosure, such as the spandex-type materials available under the designation "LYCRA®" from Invista North America of Wilmington, Del.

When the elastic layer comprises an elastic film layer, the film layer can also be made using any suitable technique. For instance, in one embodiment, the film layer can also be formed through an extrusion process.

The elastic film layer or strand layer may, for instance, employ a combination of a thermoplastic elastomer and a semi-crystalline polyolefin. Any of a variety of thermoplastic elastomers may generally be employed, such as elastomeric polyesters, elastomeric polyurethanes, elastomeric polyamides, elastomeric copolymers, and so forth, may be employed in some embodiments of the present invention. For example, the thermoplastic elastomer may be a substantially amorphous block copolymer having at least two blocks of a monoalkenyl arene polymer separated by at least one block of a saturated conjugated diene polymer. The monoalkenyl arene blocks may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth.

Particularly suitable thermoplastic elastomers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styreneolefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)--styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6937. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Other exemplary thermoplastic elastomers that may be used include polyurethane elastomeric materials such as, for example, those available under the trademark ESTANE from Noveon and LYCRA from Invista, polyamide elastomeric materials such as, for example, those available under the trademark PEBAX (polyether amide) from Atofina Chemicals Inc., of Philadelphia, Pa., and polyester elastomeric materials such as, for example, those available under the trade designation HYTREL from E.I. DuPont De Nemours & Company.

The semi-crystalline polyolefin of the elastic layer has or is capable of exhibiting a substantially regular structure. That is, semi-crystalline polyolefins may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the semi-crystalline polyolefin may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. The semi-crystalline polyolefin may also have a Vicat softening temperature of from about 10° C. to about 100° C., in some embodiments from about 20° C. to about 80° C., and in some embodiments, from about 30° C. to about 60° C. The semi-crystalline polyolefin may have a melting temperature of from about 20° C. to about 120° C., in some embodiments from about 35° C. to about 90° C., and in some embodiments, from about 40° C. to about 80° C. The latent heat of fusion ($\Delta H_f$) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Linear polyethylene plastomers that may be used in the present disclosure are ethylene-based copolymer plastomers available under the AFFINITY™ from Dow Chemical Company of Midland, Mich. Other suitable polyethylene plastomers are available under the designation ENGAGE™ from Dow Chemical Company of Midland, Mich. and EXACT™ from ExxonMobil Chemical Company of Houston, Tex. Still other suitable ethylene polymers are available from The Dow Chemical Company under the designations DOWLEX™ (LLDPE) and ATTANE™ (ULDPE). Other suitable ethylene polymers are described in U.S. Pat. Nos. 4,937,299 to Ewen et al.; 5,218,071 to Tsutsui et al.; 5,272,236 to Lai, et al.; and 5,278,272 to Lai, et al., which are incorporated herein in their entirety by reference thereto for all purposes.

Propylene polymers may also be suitable for use as a semi-crystalline polyolefin. In one particular embodiment, the semi-crystalline propylene-based polymer includes a copolymer of propylene and an α-olefin, such as a $C_2$-$C_{20}$ α-olefin or $C_2$-$C_{12}$ α-olefin. Particularly desired α-olefin comonomers are ethylene, 1-butene, 1-hexene and 1-octene. The propylene content of such copolymers may be from about 60 mole % to about 99.5 wt. %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. The distribution of the α-olefin comonomer is typically random and uniform among the differing molecular weight fractions forming the propylene copolymer. Although the density of the propylene-based polymer employed in the present invention may vary, it is typically about 0.91 grams per cubic centimeter ($g/cm^3$) or less, in some embodiments from about 0.85 to about 0.88 $g/cm^3$, and in some embodiments, from about 0.85 $g/cm^3$ to about 0.87 $g/cm^3$. The melt flow rate of the propylene-based polymer may also be selected within a certain range to optimize the properties of the resulting elastic material. The melt flow rate is the weight of a polymer (in grams) that may be forced through an extrusion rheometer orifice (0.0825-inch diameter) when subjected to a force of 2160 grams in 10 minutes at 230° C. Generally speaking, the melt flow rate is high enough to improve melt processability, but not so high as to adversely interfere with binding properties. Thus, in most embodiments of the present invention, the propylene-based polymer has a melt flow index of from about 0.1 to about 10 grams per 10 minutes, in some embodiments from about 0.2 to about 5 grams per 10 minutes, and in some embodiments, from about 0.5 to about 4 grams per 10 minutes, measured in accordance with ASTM Test Method D1238-E.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Dafta, et al.; 5,539,056 to Yang, et al.; and 5,596,052 to Resconi, et al., which are incorporated herein in their entirety by reference thereto for all purposes.

The relative amounts of the thermoplastic elastomers and semi-crystalline polyolefins are selectively controlled to achieve a balance between the mechanical and thermal properties of the elastic layer. For example, the ratio of the amount of the thermoplastic elastomer(s) to the amount of the semi-crystalline polyolefin(s) may range from about 0.5 to about 15, in some embodiments from about 1 to about 10, and in some embodiments, from about 1 to about 5. The thermoplastic elastomer(s) may constitute from about 40 wt. % to about 95 wt. %, in some embodiments from about 45 wt. % to about 90 wt. %, and in some embodiments, from about 50 wt. % to about 75 wt. % of the elastic layer. Likewise, the semi-crystalline polyolefin(s) may constitute from about 5 wt. % to about 60 wt. %, in some embodiments from about 10 wt. % to about 55 wt. %, and in some embodiments, from about 15 wt. % to about 50 wt. % of the elastic layer. It should of course be understood that other polymers may also be employed in the elastic layer. When utilized, however, the other polymers typically constitute about 10 wt. % or less, and in some embodiments, about 5 wt. % or less of the material.

In addition to polymers, the elastic layer may also employ other additives as is known in the art. For example, although the elastomeric polymers may possess a certain amount of tack, a tackifying resin may nevertheless be employed in some embodiments to facilitate subsequent bonding of the strand layer to a nonwoven web facing. One suitable class of tackifying resins includes hydrogenated hydrocarbon resins, such as REGALREZ™ hydrocarbon resins available from Eastman Chemical. Other suitable tackifying resins may be described in U.S. Pat. No. 4,787,699. When employed, the tackifying resin may be present in an amount from about 0.001 wt. % to about 35 wt. %, in some embodiments, from about 0.005 wt. % to about 30 wt. %, and in some embodiments, from 0.01 wt. % to about 25 wt. % of the elastic layer.

The elastic layer may also contain other additives as is known in the art, such as melt stabilizers, processing stabilizers, heat stabilizers, light stabilizers, antioxidants, heat aging stabilizers, whitening agents, antiblocking agents, bonding agents, viscosity modifiers, etc. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of fibers and films. Some suitable hindered phenols include those available from Ciba Specialty Chemicals of under the trade name "Irganox®", such as Irganox® 1076, 1010, or E 201. Moreover, bonding agents may also be added to facilitate bonding to additional materials (e.g., nonwoven web). When employed, additives (e.g., antioxidant, stabilizer, etc.) may each be present in an amount from about 0.001 wt. % to about 40 wt. %, in some embodiments, from about 0.005 wt. % to about 35 wt. %, and in some embodiments, from 0.01 wt. % to about 25 wt. % of the elastic layer.

As described above, the elastic layer is laminated to at least one gathered layer. For instance, in one embodiment, the elastic layer may be laminated in between a pair of opposing gathered layers. The gathered layers may comprise any suitable nonwoven material. For instance, in one embodiment, the gathered layers may comprise spunbond webs. The gathered layers, for instance, can have a basis weight of from about 5 gsm to about 120 gsm and can comprise a single layer or can comprise multiple layers.

The side areas 30 and 34 can be formed from any suitable stretchable material. The material can be non-elastic or can be elastic. The side areas 30 and 34, for instance, should at least be stretchable in a direction generally parallel to the lateral direction 49 of the chassis 12.

When formed from an elastic material, for instance, the side areas 30 and 34 can be made from any of the materials described above with respect to the front and back waistbands. In one particular embodiment, for instance, the side areas can be made from a stretch bonded laminate containing an elastic layer positioned in between two outer gathered layers.

As described above, in one embodiment, the side areas 30 and 34 can be integral with the front portion 22 and the back portion 24. In these embodiments, for instance, the entire chassis can be made from one or more elastic materials. For instance, the entire chassis can be made from any of the elastic materials described above.

As described above, the chassis 12 can generally include an outer cover, a bodyside liner, and an absorbent core. These elements of the absorbent article can be made from any suitable material depending upon the particular application.

The outer cover may be made from a material that is substantially liquid impermeable, and can be elastic, stretchable or nonstretchable. The outer cover can be a single layer of liquid and permeable material, or may include a multi-layered laminate structure in which at least one of the layers is liquid and permeable. For instance, the outer cover can include a liquid permeable outer layer and a liquid and permeable inner layer that are suitably joined together by a laminate adhesive.

For example, in one embodiment, the liquid permeable outer layer may be a spunbond polypropylene nonwoven web. The spunbond web may have, for instance, a basis weight of from about 15 gsm to about 25 gsm.

The inner layer, on the other hand, can be both liquid and vapor impermeable, or can be liquid impermeable and vapor permeable. The inner layer is suitably manufactured from a thin plastic film, although other flexible liquid impermeable materials may also be used. The inner layer prevents waste material from wetting articles such as bedsheets and clothing, as well as the wearer and caregiver. A suitable liquid impermeable film may be a polyethylene film having a thickness of about 0.2 mm.

A suitable breathable material that may be used as the inner layer is a microporous polymer film or a nonwoven fabric that has been coated or otherwise treated to impart a desired level of liquid impermeability. Other "non-breathable" elastic films that may be used as the inner layer include films made from block copolymers, such as styrene-ethylene-butylene-styrene or styrene-isoprene-styrene block copolymers.

Elastic non-woven laminate webs that can be used as the outer cover 40 include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interconnected in an integrating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, meltblown fabrics or spunbond fabrics composed of polyethylene, polypropylene, or polyolefin elastomers, as well as combinations thereof. The elastomeric materials may include PEBAX elastomer (available from AtoChem located in Philadelphia, Pa.), HYTREL elastomeric polyester (available from Invista of Wilmington, Del.), KRATON elastomer (available from Kraton Polymers of Houston, Tex.), or strands of LYCRA elastomer (available from Invista of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, embossed, and microstrained; and may be in the form of films, webs, and laminates.

In particular aspects of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik Findley Adhesive and designated as H2525A, and the elastomer strands are placed and distributed to provide approximately 12 strands of KRATON elastomer per inch (2.54 cm) of lateral width of the outer cover 40.

Alternatively, the outer cover 40 may include a woven or non-woven fibrous web layer which has been totally or partially constructed or treated to impart the desired levels of liquid impermeability to selected regions that are adjacent or proximate the absorbent core. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate material composed of a 0.6 mil (0.015 mm) thick polypropylene blown film and a 0.7 osy (23.8 gsm) polypropylene spunbond material (2 denier fibers).

Suitable materials for a biaxially stretchable outer cover 40 include biaxially stretchable material and biaxially elastic stretchable material. One example of a suitable outer cover material can include a 0.3 osy (10.2 gsm) polypropylene spunbond that is necked 60% in the lateral direction 49 and creped 60% in the longitudinal direction 48, laminated with 3 grams per square meter (gsm) Findley 2525A styrene-isoprene-styrene based adhesive to 8 gsm PEBAX 2533 film with 20% $TiO_2$ concentrate. The outer cover 40 can suitably be stretched, laterally and/or longitudinally, by at least 30% (to at least 130% of an initial (unstretched) width and/or length of the outer cover 40). More suitably, the outer cover 40 can be stretched laterally and/or longitudinally, by at least 50% (to at least 150% of the unstretched width or length of the outer cover 40). Even more suitably, the outer cover 40 can be stretched, laterally and/or longitudinally, by at least 100% (to at least 200% of the unstretched width or length of the outer cover 40). Tension force in the outer cover 40 at 50% extension is suitably between 50 and 1000 grams, more suitably between 100 and 600 grams, as measured on a 3 inch (7.62 cm) wide piece of the outer cover material.

Another example of a suitable material for a biaxially stretchable outer cover 40 is a breathable elastic film/non-woven laminate, described in U.S. Pat. No. 5,883,028, issued to Morman et al., incorporated herein by reference to the extent that it is consistent (i.e. not in conflict) herewith. Examples of materials having two-way stretchability and retractability are disclosed in U.S. Pat. No. 5,116,662 issued to Morman and U.S. Pat. No. 5,114,781 issued to Morman, both of which are hereby incorporated herein by reference to the extent that it is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

As described above, the absorbent core is positioned in between the outer cover and a liquid permeable bodyside liner. The bodyside liner is suitably compliant, soft feeling, and non-irritating to the wearer's skin. The bodyside liner can be manufactured from a wide variety of web materials, such as synthetic fibers, natural fibers, a combination of natural and synthetic fibers, porous foams, reticulated foams, apertured plastic films, or the like. Various woven and nonwoven fabrics can be used for the bodyside liner. For example, the bodyside liner can be made from a meltblown or spunbonded web of polyolefin fibers. The bodyside liner can also be a bonded-carded web composed of natural and/or synthetic fibers.

The bodyside liner may be constructed to be extensible but not elastic. In other embodiments, however, the liner may be configured to be elastic in the longitudinal direction, in the transverse direction, or in both directions.

A suitable liquid permeable bodyside liner is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber. In this particular embodiment, the polypropylene forms the core and the polyethylene forms the sheath of the fiber. Other fiber orientations, however, are possible.

As described above, in one embodiment, the bodyside liner can be stretchable and elastic, especially when the side areas are constructed integral with the chassis. Suitable elastomeric materials for construction of the bodyside liner 42 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably includes a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials may be extensible biaxially stretchable materials, such as a neck stretched/creped spunbond. The bodyside liner 42 can also be made from extensible materials as are described in U.S. Pat. No. 6,552,245 filed on May 3, 2000 by Roessler et al which is incorporated herein by reference. The bodyside liner 42 can also be made from biaxially stretchable materials as are described in U.S. Pat. No. 6,969,378 filed on Oct. 27, 2000 by Vukos et al which is incorporated herein by reference.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). Even more suitably, the liner 42 can be stretched, laterally and/or longitudinally, by at least 100% (to at least 200% of the unstretched width or length of the liner 42). Tension force in the liner 42 at 50% extension is suitably between 50 and 1000 grams, more suitably between 100 and 600 grams, as measured on a 3 inch (7.62 cm) wide piece of the liner material.

The material used to form the absorbent core, for example, may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 90 weight percent based on total weight of the web. The web may have a density within the range of about 0.1 to about 0.45 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 15 times its weight in liquid, and suitably is capable of absorbing more than about 25 times its weight in liquid. Suitable superabsorbent materials are readily available from various suppliers. For example, FAVOR SXM 880 superabsorbent is available from Stockhausen, Inc., of Greensboro, N.C., USA; and Drytech 2035 is available from Dow Chemical Company, of Midland, Mich., USA.

In addition to cellulosic fibers and superabsorbent materials, the absorbent pad structures may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent core, and alternatively or additionally may provide adherence between facing layers of the folded structure.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be used. For example, an elastomeric coform absorbent core may be used to form the absorbent core according to the invention. Examples of such elastomeric coform materials are provided in U.S. Pat. No. 5,645,542, incorporated herein in its entirety for all purposes. As another example, a suitable absorbent elastic nonwoven material may include a matrix of thermoplastic elastomeric nonwoven filaments with the matrix including a plurality of absorbent fibers and a super-absorbent material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.1 to about 0.45 grams per cubic centimeter. The absorbent web can alternatively be a foam.

Absorbent articles made in accordance with the present disclosure can be used in numerous applications. For instance, the absorbent articles can be used as a diaper, a training pant, a feminine hygiene product, and the like. In one particular embodiment, for instance, the absorbent article may comprise an adult incontinence product.

Referring to FIGS. 3 and 4, other components that may be contained in the absorbent article 10 are shown. For instance, as shown particularly in FIG. 4, in one embodiment, the absorbent article can include elasticized containment flaps 46 that are attached to the liner 42. The containment flaps 46 define a partially unattached edge which assumes an upright configuration in at least the crotch region 26 of the absorbent article 10 to form a seal against the wearer's body. The containment flaps 46 can extend longitudinally along the entire length of the chassis 12 or may extend only partially along the length of the chassis. Suitable constructions and arrangements for the containment flaps 46 are generally well known to those skilled in the art and are described in U.S. Pat. No. 4,704,116, which is incorporated herein by reference.

To further enhance containment and/or absorption of body exudates, the absorbent article 10 may also include leg elastic members 58. The leg elastic members 58 can be operatively joined to the outer cover 40 and/or the bodyside liner 42 and positioned in the crotch region 26 of the absorbent article 10. The leg elastic members can be made from any suitable elastic material such as any of those described above with respect to the waistbands 54 and 56.

As shown in FIGS. 3 and 4, the side areas 30 and 34 each have a longitudinal outer edge 68 and a leg end edge 70 disposed towards the longitudinal center of the absorbent article 10, and waist edges 72 disposed toward a longitudinal end of the article. The leg end edges 70 and the outer edges 68 of the side areas form part of the pant side edges 36 of the absorbent article 10. The leg end edges 70 may be suitably curved and/or angled relative to the lateral direction 49 to provide a better fit around the wearer's legs. The waist end edges 72 form a front waist edge and a back waist edge of the article.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. An absorbent article comprising:
   a chassis defining two leg openings opposite a waist opening, the chassis containing an absorbent core and including a front portion, a back portion and a crotch portion positioned in between the front portion and the back portion, the chassis further including first and second opposing elastic side areas, the first elastic side area including a first panel attached to a second panel along a first vertical attachment area and wherein the second side area also includes a first panel attached to a second panel along a second vertical attachment area;
   a back elastic waistband that partially encircles the waist opening of the chassis, the back waistband having a first end and a second end, the first end terminating on the first panel of the first side area but leaving a gap between the first end and the first vertical attachment area such that the gap is entirely defined on the first panel of the first elastic area, the second end terminating on the first panel of the second side area but also leaving a gap between the second end and the second vertical attachment area such that the gap is entirely defined on the first panel of the second side area; and
   a front elastic waistband that partially encircles the waist opening of the chassis, the front waistband having a first end and a second end, the first end of the front waistband terminating on the second panel of the first side area but leaving a gap between the first end and the first vertical attachment area such that the gap is entirely defined on the second panel of the first side area, the second end of the front waistband terminating on the second panel of the second side area and also leaving a gap between the second end and the second vertical attachment area such that the gap is entirely defined on the second panel of the second side area,
   wherein the chassis includes an interior surface configured to face the wearer and an exterior surface facing away from the wearer, the back or front waistband being affixed on the interior surface of the article with the other waistband being affixed on the exterior surface of the article facing away from the wearer,
   wherein a surface of the elastic waistband facing the chassis is attached to the chassis along a length of the waistband such that the waistband remains affixed to a layer below the interior surface of the chassis closest to a wearer during use,
   wherein the gaps between the first end of the back waistband and the first vertical attachment area, between the second end of the back waistband and the second vertical attachment area, between the first end of the front waistband on the first vertical attachment area, and between the second end of the front waistband and the second vertical attachment area are from about 3 mm to about 80 mm such that the gap creates a hinge point between the respective waistband ends and the respective vertical attachment areas.

2. An absorbent article as defined in claim 1, wherein the first and second panels of each side area are permanently attached together along the vertical attachment area to form a seam.

3. An absorbent article as defined in claim 1, wherein the first and second side panels of each of the side areas are releasably attached together along the vertical attachment area.

4. An absorbent article as defined in claim 3, wherein the first and second panels of each side area are attached together using a mechanical fastener.

5. An absorbent article as defined in claim 4, wherein the mechanical fastener comprises a hook and loop fastener.

6. An absorbent article as defined in claim 3, wherein the mechanical fastener comprises an adhesive fastener.

7. An absorbent article as defined in claim 1, wherein the gap between the first end of the back or front waistband and the first vertical attachment area and the gap between the second end of the back or front waistband and the second vertical attachment area is from about 10 mm to about 50 mm.

8. An absorbent article as defined in claim 1, wherein each of the first panels of the side areas has a length along a lateral direction of the chassis, the back or front waistband extending over at least 25% of the length of each of the first panels.

9. An absorbent article as defined in claim 8, wherein the panels that comprise the first and second side areas have a length that extend in a lateral direction of the chassis, the back and front waistbands extending over at least 30% of the length of a respective panel.

10. An absorbent article as defined in claim 1, wherein the back or front waistband comprises an elastic film, an elastic nonwoven layer, or an elastic woven layer.

11. An absorbent article as defined in claim 1, wherein the first and second side areas, the back waistband, and the front waistband are all made from elastic laminates.

12. An absorbent article as defined in claim 11, wherein the back or front waistband comprises a stretch bonded laminate.

13. An absorbent article as defined in claim 12, wherein the stretch bonded laminate comprises an elastic layer positioned in between two gathered layers.

14. An absorbent article as defined in claim 1, wherein the chassis defines a waist edge surrounding the waist opening, the back or front waistband being positioned adjacent to the waist edge.

15. An absorbent article as defined in claim 1, wherein the chassis includes a functional product width in the lateral direction along the front portion and a functional product width in the lateral direction along the back portion, and wherein the length of the back elastic waistband or front elastic waistband to functional product width is from about 45% to about 95%.

16. An absorbent article as defined in claim 15, wherein the functional product width is measured laterally from an inside edge of a first fastener mechanism located on one side of the article to an inside edge of a second fastener mechanism located on an opposite side of the article.

17. An absorbent article as defined in claim 1, wherein the first and second side areas, the back waistband, and the front waistband, all have a width in a longitudinal direction of the chassis and wherein the width of the back waistband and the width of the front waistband are from about 15% to about 125% of the width of the side areas.

18. An absorbent article as defined in claim 1, wherein the first and second side areas are integral with the chassis and wherein the chassis is formed from at least one elastic material such that the chassis can be stretched in a lateral direction at least 30%.

* * * * *